United States Patent
Allen et al.

(10) Patent No.: US 6,677,328 B1
(45) Date of Patent: Jan. 13, 2004

(54) METHOD FOR THE PREVENTION OF COLONIC ADENOMAS

(75) Inventors: Carroll Wayne Allen, Chatham, NJ (US); Thomas Albert Brasitus, Olympia Fields, IL (US); David Lewis Earnest, Tuscon, AZ (US); Gerald Leigh Messerschmidt, Mendham, NJ (US)

(73) Assignees: Novartis Corp., New York City, NY (US); University of Chicago, Chicago, IL (US); University of Arizona, Tucson, AZ (US)

(*) Notice: Subject to any disclaimer, the term of this patent is extended or adjusted under 35 U.S.C. 154(b) by 0 days.

(21) Appl. No.: 09/691,496

(22) Filed: Oct. 18, 2000

Related U.S. Application Data

(63) Continuation of application No. 09/384,642, filed on Aug. 27, 1999, which is a continuation of application No. 08/887,682, filed on Jul. 3, 1997, now abandoned, which is a continuation of application No. 08/430,653, filed on Apr. 28, 1995, now abandoned.

(51) Int. Cl.$^7$ ............................................... A61K 31/56
(52) U.S. Cl. ........................ 514/182; 514/169; 424/489; 424/490; 424/451; 424/472
(58) Field of Search ................. 424/489, 490, 424/472, 451; 514/169, 182

(56) References Cited

U.S. PATENT DOCUMENTS

| | | | |
|---|---|---|---|
| 4,859,660 A | 8/1989 | Poupon | 514/182 |
| 5,814,625 A | 9/1998 | Larson et al. | 514/171 |
| 5,843,929 A | 12/1998 | Larson et al. | 514/182 |
| 5,945,411 A | 8/1999 | Larson et al. | 14/171 |

OTHER PUBLICATIONS

Chemoprevention of Azoxymethane–induced Colonic Carcinogenesis by Supplemental Dietary Ursodeoxycholic Acid by David L. Earnest etal.—Cancer Research 54, 5071–5074, Oct. 1, 1994.

The effect of bile acids and piroxicam on MHC antigen expression in rat colonocytes during colon cancer development by B. Rigas, et al.—Immunology 1994 83 319–323.

Increase by Deoxychloric Acid of the Colonic Nuclear Damage Induced by Known Carcinogens in C57BL/6J Mice by Kunio Suzuki and W. Robert Bruce—JNCI, vol. 76, No. 6, Jun. 1986.

Faecal bile acid concentrations of patients with carcinoma or increased risk of carcinoma in the large bowel by D. G Mudd et al., Gut, 1980, 21, 587–590.

Metabolic Epidemiology of Colon Cancer Fecal bile Acids and Neutral Sterols in Colon Cancer Patients and Patients with Adenomatous Polyps by Bandaru S. Reddy, DVM, PhD and Ernst L. Wynder, MD—Cancer 39:2533–2539, 1977.

Selective preservation of protein C–ζ in the chemoprevention of azoxymethane–induced colonic tumors by piroxicam by Hermant K. Roy et al.—FEBS Letter 366 (1995) 143–145.

Acute Effects of Ursodeoxychloric and Chenodeoxycholic Acid on the Small Intestinal Absorption of Bile Acids by A. Stiehl, R. Raedsch and G. Rudolph—Gastroenterology 1990; 98: 424–428.

*Primary Examiner*—Thurman K. Page
*Assistant Examiner*—Konata M George
(74) *Attorney, Agent, or Firm*—Joseph J. Borovian; Gregory D. Ferraro

(57) ABSTRACT

Method for the prevention of colonic adenomas in mammals at risk of developing them by administering to such mammals an effective colonic adenoma preventive amount of ursodiol or a pharmaceutically acceptable salt conjugation product thereof.

18 Claims, No Drawings

METHOD FOR THE PREVENTION OF COLONIC ADENOMAS

This is a continuation of U.S. patent application Ser. No. 09/384,642, filed Aug. 27, 1999, which application is a continuation of U.S. patent application Ser. No. 08/887,682, filed Jul. 3, 1997, which application is a continuation of U.S. patent application Ser. No. 08/430,653, filed Apr. 28, 1995, the latter two of which are now abandoned.

This invention relates to research that was conducted partially with funding from National institutes of Health Grants CA36745 and DK42086 and the Federal Government may have certain rights in the invention.

FIELD OF THE INVENTION

The invention relates to the area of precancerous cell formation in the colon in those patients at risk for developing such precancerous cells. It also relates to preventing recurrence of such cell formation in those having been treated for cancer of the colon.

BACKGROUND OF THE INVENTION

Cancer of the colon is a common and deadly disease in the Western world. Genetic predisposition plays an important role, but exposure to substances that initiate and promote cancer is essential for a malignant tumor to develop. Bile acids have been implicated as important cancer-promoting agents.

In the normal colon mucosa, epithelial cells line crypts along the mucosal wall. Those epithelial cells which line the colon exposed surface and approximately the upper ⅔ of the crypt are normally non-proliferating, while those lining the lower ⅓ of the crypts are proliferating. As the proliferating cells migrate toward the upper portion of the crypt they transform and lose their proliferative ability. Ultimately the oldest cells are shed from the colon surface in the normal functioning of the colon. However, when the proliferating epithelial cells are induced to retain their proliferative capacity after reaching the upper ⅓ of the crypt, the normal process may go awry and microadenomas form. The proliferating cell, now at the surface of the colon continues to proliferate and a polyp develops.

Polyps may be either benign or cancerous. Some never become cancerous, but it is believed that adenomatous polyps are the main precursors of colon cancer and that about 90% of colon cancers develop from adenomatous polyps. Most adenomas do not continue to grow in size, but those that do are more likely to develop malignant changes. Therefore, reducing the number of adenomas and/or preventing their growth substantially reduces the number of potential colon cancers in the future.

Since subjects once treated for colon cancer have a much greater risk for developing further adenomas and cancers, potential adenoma prevention is extremely valuable in this population. The same may be said for close blood relatives of those treated for colon cancer, who may be at increased risk for adenoma and colon cancer cancer development.

Bile acids have been implicated as important cancer promoting agents. In the normal sequence of events, bile acids are conjugated with taurine and glycine, making them more hydrophilic. It is these conjugated bile acids that are primarily involved in the digestion of fat. The bulk of these are reabsorbed in the final segment of the small bowel. However some of the conjugated bile acids are not absorbed and pass further down the GI tract.

Bacterial modification of the conjugated bile acids occurs in the lower intestine or colon. Two primary pathways are involved, deconjugation and dehydroxylation. Free bile acids are produced from the conjugate and removal of the 7-alpha hydroxyl group results in formation of secondary bile acids. Each of these steps changes the bile acid to a more lipophilic compound and to one which is more cytotoxic and more cancer promoting than the unmodified compound.

Normal fecal bile acids in healthy adults have been reported as:

| | | |
|---|---|---|
| Deoxycholic acid | 45%–55% | (more lipophilic) |
| Lithocholic acid | 30%–40% | (more lipophilic) |
| Cholic acid | 3%–5% | (more hydrophilic) |
| Chenodeoxycholic acid | 3%–5% | |
| Conjugated bile acids | <5% | (more hydrophilic) |
| Oxo bile acids | variable | |
| Unsaturated bile acids | <1% | |

The normal healthy control is believed to have a proper balance of bile acids. If the lipophilic/hydrophilic balance of the bile acid pool is significantly upset in the lipophilic direction, the bile acids may become toxic or harmful to the colonic epithelial cells. It is believed that as the lipophilic nature of the bile acid pool increases, the mucosal epithelial cells are more likely to be damaged by the presence of the secondary bile acids, especially deoxycholate. The damaged cells then begin the repair process which includes inducing cell proliferation. Repeated and frequent damage repeatedly induces proliferation and repair. The process of apoptosis or programmed cell death may also be affected. Research in rats has shown that excessive lipophilic bile acids in the colon can impair apoptosis and possibly increase the risk of forming adenomas and cancer. In addition, once the cell membrane has been compromised, agents which would not affect or which would have a difficult time affecting the colonic mucosal epithelial cells are more likely to have a significant impact.

OBJECTS OF THE INVENTION

It is therefore an object of the present invention to provide a method of preventing formation and/or growth of adenomas and microadenomas as precursor lesions of cancer.

It is another object of the invention to provide a method of protecting colonic mucosal epithelial cells from the damaging affects of an overly lipophilic bile acid pool exposure.

It is still another object of the invention to provide a method of treating patients having a high risk of adenoma development so as to lower that risk.

SUMMARY OF THE INVENTION

These and other objects of the invention are achieved by administering an effective adenoma or microadenoma preventing amount of ursodiol or a pharmaceutically acceptable salt or a pharmaceutically acceptable conjugate thereof to a mammal in need of such treatment.

DETAILED DESCRIPTION OF THE INVENTION

The instant invention is a method of preventing adenomas or microadenomas in a mammal at risk of developing such adenomas or microadenomas comprising administering to such mammal an effective adenoma and/or microadenoma preventing amount of ursodiol or a pharmaceutically acceptable salt or a pharmaceutically acceptable conjugate thereof in one or more divided doses.

Ursodiol is ursodeoxycholic acid (chemical name: 3-α-7-β-dihydroxy-5-β-cholan-24-oic acid), and is commercially available in pharmaceutical a dosage form under the name ACTIGALL® (Summit Pharmaceuticals, a division of Ciba-Geigy Corporation). Pharmaceutically acceptable salts of ursodiol include the alkali metal (preferably sodium and potassium) and alkaline earth metal (preferably calcium and magnesium) salts; most preferably sodium or potassium salts. Pharmaceutically acceptable conjugates of ursodiol include conjugates thereof with glycine or taurine. Preferably, free ursodiol is used in the present invention.

While any mammal may be treated with the present invention, the invention is primarily directed toward humans, farm animals, and pets; most preferably humans. Since ursodiol is, in part, metabolized to lithocholic acid, a liver toxin, mammals treated in accordance with the present invention should be capable of detoxifying lithocholic acid and removing it from the body. In humans, this is reasonably efficiently carried out by the process of sulfation and conjugation, with elimination in the feces and urine. Those of ordinary skill in the art (particularly in veterinary medicine) will be able to determine whether a particular species is capable of processing lithocholic acid to avoid any significant liver damage from the instant process.

For purposes of the present invention, the at risk population of one or more of the mammals to be treated includes those (1) having been diagnosed with colon cancer, colonic adenomas, and/or colonic microadenomas; and/or (2) having a close blood relative who has been diagnosed with colon cancer, colonic adenomas, and/or colonic microadenomas.

For purposes of the present invention the effective amount of ursodiol, its salts and its conjugates is calculated on the amount of ursodiol and is from about 1 mg/kg/day orally to about 30 mg/kg/day orally; preferably about 5 mg/kg/day to about 20 mg/kg/day; more preferably, about 8 mg/kg/day to about 10 mg/kg/day. The dosage may be in 1 or more divided doses. Typically, the daily dose is given in 1–4, preferably 2–3 divided doses. Typical doses for an adult human of about 60 kg is 300 mg of ursodiol from 1 to 4 times, preferably 1–3 times, most preferably 2–3 times a day.

The active agent may be given in a variety of dosage forms, although commercially available ursodiol capsules, under the name ACTIGALL® are most suitable for adult humans.

When necessary or desirable, the active agent can be formulated with standard excipients and appropriate coating materials to obtain immediate release, controlled release or sustained release dosage forms. Such excipients include, but are not limited to: titanium dioxide, talc; starch; microcrystalline cellulose, microgranular cellulose, casein formaldehyde, colloidal silicon dioxide; lubricants such as magnesium stearate; colorants such as iron oxide; Eudragit coating materials, polyvinyl pyrrolidone, polyethyleneglycols, alumina, carboxymethylcellulose, and gelatin. Alternative specific formulations are disclosed in U.S. Pat No. 3,859,437; and U.S. Pat. No. 4,263,272. Still other formulations will be readily apparent to those of ordinary skill in the pharmaceutical formulation art.

EXAMPLE

Example 1

Male Fischer 344 rats are fed a standard AIN-76 diet supplemented as indicated in the table below. The control group diet is not supplemented at all. After 2 weeks, half of the rats in each group receive azoxymethane (15 mg/kg) or azoxymethane vehicle subcutaneously once a week for two weeks. Azoxymethane is a known colon cancer inducer and the object of the experiment is to demonstrate the effect of ursodiol on reduction of the number of adenomas and the reduction of the number of adenomas that progress on toward malignancy. After 28 weeks, the rats are sacrificed, the colons harvested and examined for neoplasms. None of the rats injected with azoxymethane vehicle develop tumors. The results are shown in the table below. Since it is believed that malignancies develop from adenomas, the total tumor bearing rat values are particularly enlightening as this represents the number of growths that are still in the adenoma stage and the number of growths that have continued to progress to cancers. Ursodiol reduced the number of growths from control by 50%, with a 100% reduction in those that progressed to cancers and a 33% reduction in the number of tumors that still remained as adenomas. Cholic acid, as expected as an promoter of colon cancer, increased the number of malignancies over control. Interestingly, cholic acid also increased the number of adenomas which were present, consistant with the concept that increased numbers of adenomas are likely to lead to increased risk of colon cancer development. Piroxicam also reduced both adenomas and malignancies, but neither was reduced as dramatically as seen with ursodiol administration.

| DIET | NO. RATS | TUMOR BEARING RATS {%} | | |
|---|---|---|---|---|
| | | BENIGN (ADENOMA) | MALIGNANT (CANCERS) | TOTAL |
| Control | 43 | 14 {33} | 6 {14} | 20 {47} |
| Cholic Acid 0.4% | 47 | 20 {43} | 14 {30} | 34 {73} |
| Ursodiol 0.4% | 45 | 10 {22} | 0 {0} | 10 {22} |
| Piroxicam 75 ppm | 56 | 16 {29} | 3 {5} | 19 {34} |

Example 2

The procedure of Example 1 was followed except that the number of rats involved are as stated in the table below and aberrant crypt frequency was examined upon sacrifice of the rats. The incidence of microadenomas, adenomas, and cancers in the tested populations was recorded and appears in the table below.

| DIET | NO. RATS | TUMOR BEARING RATS | | | |
|---|---|---|---|---|---|
| | | BENIGN | | MALIGNANT (CANCERS) | TOTAL |
| | | (MICRO-ADENOMA) | (ADENOMA) | | |
| Control | 24 | 30 | 43 | 13 | 86 |
| Cholic Acid (0.4%) | 23 | 57 | 71 | 38 | 166 |
| Piroxicam | 24 | 25 | 42 | 8 | 75 |
| Ursodiol (0.4%) | 22 | 23 | 27 | 0 | 50 |

These results demonstrate that ursodiol not only reduces the incidence of malignancies, but also reduces both the number and size of the non-cancerous or pre-cancerous growths.

Example 3

The procedure of Example 1 was followed except that 31–56 rats were assigned to one of 7 diets as indicated in the table below. After 2 weeks 20–32 of the rats in each group were given subcutaneous injections of azoxymethane (15 mg/kg) once a week for 2 weeks, while 7–24 rats received subcutaneous injection of the vehicle only. The results are shown in the table below.

| DIET | NO. RATS | TUMOR BEARING RATS | | |
|---|---|---|---|---|
| | | BENIGN | MALIGNANT | TOTAL |
| Study center 1 | | | | |
| Control (SD) | 20 | 7 | 3 | 10 |
| SD + Cholic Acid (0.2%) | 23 | 12 | 4 | 16 |
| SD + Cholic Acid (0.4%) | 23 | 12 | 5 | 17 |
| SD + Urso (0.2%) | 24 | 8 | 5 | 13 |
| SD + Urso (0.4%) | 23 | 4 | 0 | 4 |
| SD + Cholic Acid (0.2%) + Urso (0.2%) | 24 | 7 | 4 | 11 |
| SD + Piroxicam | 32 | 8 | 1 | 9 |
| Study Center 2 | | | | |
| Control (SD) | 23 | 7 | 3 | 10 |
| SD + Cholic Acid (0.2%) | 24 | 6 | 8 | 14 |
| SD + Cholic Acid (0.4%) | 24 | 8 | 9 | 17 |
| SD + Urso (0.2%) | 24 | 6 | 4 | 10 |
| SD + Urso (0.4%) | 22 | 6 | 0 | 6 |
| SD + Cholic Acid (0.2%) + Urso (0.2%) | 23 | 1 | 8 | 9 |
| SD + Piroxicam | 24 | 8 | 2 | 10 |

These studies show that the effect of ursodiol in preventing the development of tumors does not seem to be as strong as lower concentrations of ursodiol, i.e., 0.2%.

We claim:

1. A method for the reduction of the incidence of colonic adenomas and colonic microadenomas in a mammal at risk of developing such adenomas or microadenomas, wherein such mammal is selected from the group consisting of those mammals which (a) have been diagnosed with colon cancer, colonic adenomas, colonic microadenomas or colonic polyps and (b) have a close blood relative diagnosed with colon cancer, colonic adenomas, colonic microadenomas or colonic polyps comprising
   administering to said mammal an active agent selected from the group consisting of ursodiol; a pharmaceutically acceptable salt of ursodiol, and a pharmaceutically acceptable conjugate of ursodiol, wherein said active agent is administered in an amount effective for reducing the incidence of adenoma or microadenoma in said mammal.

2. The method of claim 1 wherein said mammal is selected from the group consisting of farm mammals, household pets, and humans.

3. The method of claim 1 wherein the mammal is human.

4. The method of claim 1 wherein said active agent is ursodiol.

5. The method of claim 1 wherein said effective amount is from about 1 mg/kg/day to about 30 mg/kg/day orally calculated on the basis of free ursodiol.

6. The method of claim 1 wherein said effective amount is from about 8 mg/kg/day to about 10 mg/kg/day.

7. The method of claim 1 wherein said daily dose of said active agent is administered in from 1 to 4 divided doses.

8. The method of claim 1 wherein said daily dose of said active agent is administered in from 2 to 3 divided doses.

9. A method for reducing the incidence of colonic adenomas and colonic microadenomas in a mammal at risk of developing such adenomas or microadenomas comprising:
   selecting a subject mammal from the group consisting of those mammals which (a) have been diagnosed with colon cancer, colonic adenomas, colonic microadenomas or colonic polyps and (b) have a close blood relative diagnosed with colon cancer, colonic adenomas, colonic microadenomas or colonic polyps and
   administering to said subject an active agent selected from the group consisting of ursodiol, a pharmaceutically acceptable salt or ursodiol, and a pharmaceutically acceptable conjugate of ursodiol, wherein said active agent is administered in an amount effective for reducing the incidence of colonic microadenomas or colonic adenomas in said subject.

10. The method of claim 9 wherein said mammal is human.

11. The method of claim 9 wherein said active agent is free ursodiol.

12. The method of claim 9 wherein said effective amount is from about 1 mg/kg/day to about 30 mg/kg/day orally calculated on the basis of free ursodiol.

13. The method of claim 12 wherein said effective amount is from about 8 mg/kg/day to about 10 mg/kg/day.

14. The method of claim 9 wherein said daily dose of said active agent is administered in from 1 to 4 divided doses.

15. The method of claim 14 Wherein said daily dose of said active agent is administered from 2 to 3 divided doses.

16. The method for reducing the incidence of colon cancer in a mammal at risk of developing colon cancer comprising:
   selecting a subject mammal from the group consisting of those mammals which (a) have been diagnosed with colon cancer, colonic adenomas, colonic microadenomas or colonic polyps and (b) have a close blood relative diagnosed with colon cancer, colonic adenomas, colonic microadenomas or colonic polyps; and
   administering to said subject an active agent selected from the group consisting of ursodiol, a pharmaceutically acceptable salt of ursodiol, and a pharmaceutically acceptable conjugate of ursodiol, wherein said active agent is administered in an amount effective for reducing the incidence of colonic microadenomas or colonic adenomas in said subject.

17. A method of lowering the risk of adenoma development in a patient at high risk of such development, comprising administering to said patient an effective adenoma risk lowering amount of an active agent selected from the group consisting of ursodiol, a pharmaceutically acceptable salt of ursodiol, and a pharmaceutically acceptable conjugate of ursodiol.

18. The method of claims 1–8, 9–15, 16 or 17 wherein said method does not require determining that the mammal has a bile acid deficiency.

* * * * *